US00PP29234P3

(12) United States Plant Patent
Hansen et al.

(10) Patent No.: US PP29,234 P3
(45) Date of Patent: Apr. 10, 2018

(54) ***MONARDA* PLANT NAMED 'PARDON MY CERISE'**

(50) Latin Name: *Monarda didyma*
Varietal Denomination: Pardon My Cerise

(71) Applicants: Hans A. Hansen, Zeeland, MI (US); Kevin A. Hurd, Austin, TX (US)

(72) Inventors: Hans A. Hansen, Zeeland, MI (US); Kevin A. Hurd, Austin, TX (US)

(73) Assignee: Walters Gardens Inc, Zeeland, MI (US)

( * ) Notice: Subject to any disclaimer, the term of this patent is extended or adjusted under 35 U.S.C. 154(b) by 40 days.

(21) Appl. No.: 14/998,971

(22) Filed: Mar. 10, 2016

(65) Prior Publication Data

US 2017/0265370 P1 Sep. 14, 2017

(51) Int. Cl.
*A01H 5/02* (2018.01)

(52) U.S. Cl.
USPC ..... Plt./455

(58) Field of Classification Search
USPC ..... Plt./455
See application file for complete search history.

(56) References Cited

PUBLICATIONS

UPOV hit on *Monarda* plant named 'Pardon My Spirit', CA PBR 16-8799, Jan. 22, 2016.*

* cited by examiner

*Primary Examiner* — Anne Marie Grunberg

(57) ABSTRACT

The new and distinct cultivar of ornamental bee balm plant named *Monarda didyma* 'Pardon My Cerise' has short, compact, basally branching stems, medium to dark green foliage with slight tinting of greyed purple, numerous large cerise-colored flowers creating excellent flower coverage and strong foliar resistance to powdery mildew.

1 Drawing Sheet

Botanical classification: *Monarda didyma.*
Variety denomination: 'Pardon My Cerise'.

BACKGROUND OF THE INVENTION

The present invention relates to the new and distinct cultivar of bee balm plant, botanically known as *Monarda didyma* 'Pardon My Cerise', and hereinafter also referred to solely as the cultivar 'Pardon My Cerise' or the "new plant". The new plant was selected from seed collected by the hybridizers on Oct. 7, 2009 from designated hybridizing plot of a nursery in Zeeland, Mich., USA, from *Monarda didyma* 'Petite Delight' U.S. Plant Pat. No. 10,784 as the female or seed parent and the male or pollen parent was uncontrolled and could have been any of the other parents in a large collection in the nearby vicinity. The plant was a single selection originally made in the summer of 2011 from the seeds that were sown in the fall of 2009. Further selection was completed in the trial fields of a nursery in Zeeland, Mich. in the summer of 2012 and the plant was assigned the breeder code of HK9-42-16. The plant has been asexually propagated by shoot tip cuttings originally in 2012 at the same nursery in the greenhouses in Zeeland, Mich., and the subsequent asexually propagated plants found to be stable, true to type and identical to the original selection.

No plants of *Monarda* 'Pardon My Cerise' have been sold in this country, or anywhere in the world, prior to the filing of this application, nor has any disclosure of the new plant been made prior to the filing of this application with the exception of that which was disclosed within one year of the filing of this application and was either derived directly or indirectly from the inventors.

BRIEF SUMMARY OF THE PLANT

*Monarda didyma* 'Pardon My Cerise' is unique from its parents and all other bee balm plants known to the inventors. The nearest comparison varieties are the female parent 'Petite Delight', 'Achall' U.S. Plant Pat. No. 19,582 and 'Fire Marshall' U.S. Plant Pat. No. 23,286. 'Petite Delight' is in similar in height, but that the new plant has flowers that are more cerise than the pink of 'Petite Delight'. The flowers of 'Achall' are more red-purple than the cerise of 'Pardon My Cerise', but the two are close in height. 'Jacob Cline' (not patented), 'Colrain Red' (not patented), 'Cambridge Scarlet' (not patented), 'Gardenview Scarlet' (not patented), 'Marshalls Delight' (not patented), 'Fireball' U.S. Plant Pat. No. 14,235 and 'Fire Marshall' U.S. Plant Pat. No. 23,286 all have similar reddish or cerise flower colors. 'Jacob Cline', 'Colrain Red', 'Cambridge Scarlet', 'Gardenview Scarlet', 'Marshalls Delight' and 'Fireball' are all taller with heights of about 120 cm, 90 cm, 95 cm, 90 cm, 70 cm and 60 cm respectively. 'Fire Marshall' has a height of about 50 cm compared to the shorter height of 'Pardon My Cerise' of about 45 cm. 'Pardon My Cerise' also has darker green-colored foliage than 'Fire Marshall'. Other similar-sized or smaller bee balm include 'Pardon My Pink' U.S. Plant Pat. No. 24,244 which has a much more pinkish flower than the new plant, and 'Pardon My Purple' U.S. Plant Pat. No. 22,170 which has a much more purplish flower than the new plant.

The following are traits of *Monarda didyma* 'Pardon My Cerise' that in combination distinguish it from all other bee balm known to the inventor:

1. Very short, winter-hardy, compact, clumping habit.

2. Medium to dark-green leaves with tinting of greyed purple.
3. Strong powdery mildew resistant foliage.
4. Large-sized, cerise-colored flowers for a long period in summer with excellent flower coverage.

BRIEF DESCRIPTION OF THE DRAWINGS

The photographs of the new plant demonstrate the unique traits of 'Pardon My Cerise' and the overall appearance of the plant at two-years old in the full sun trial garden of a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
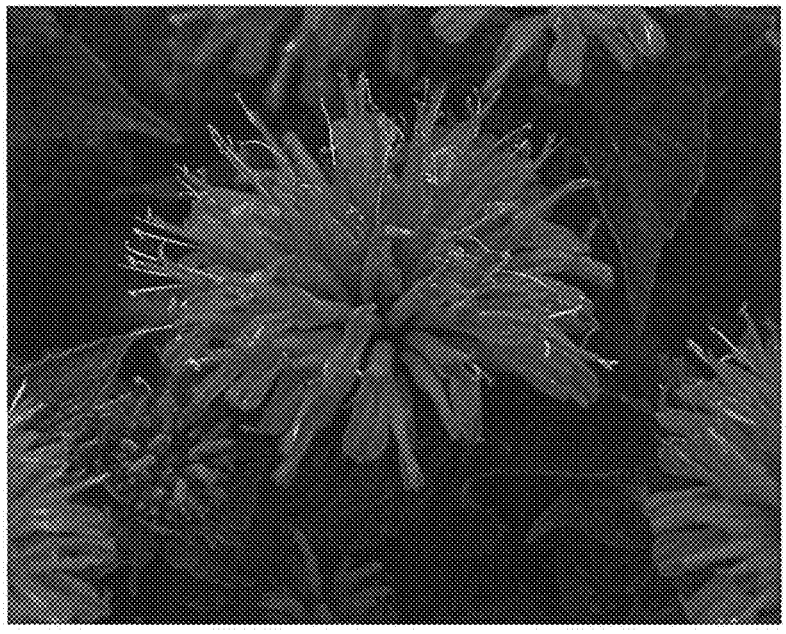
FIG. 1 shows a close-up of the flowers.
Figure 2:
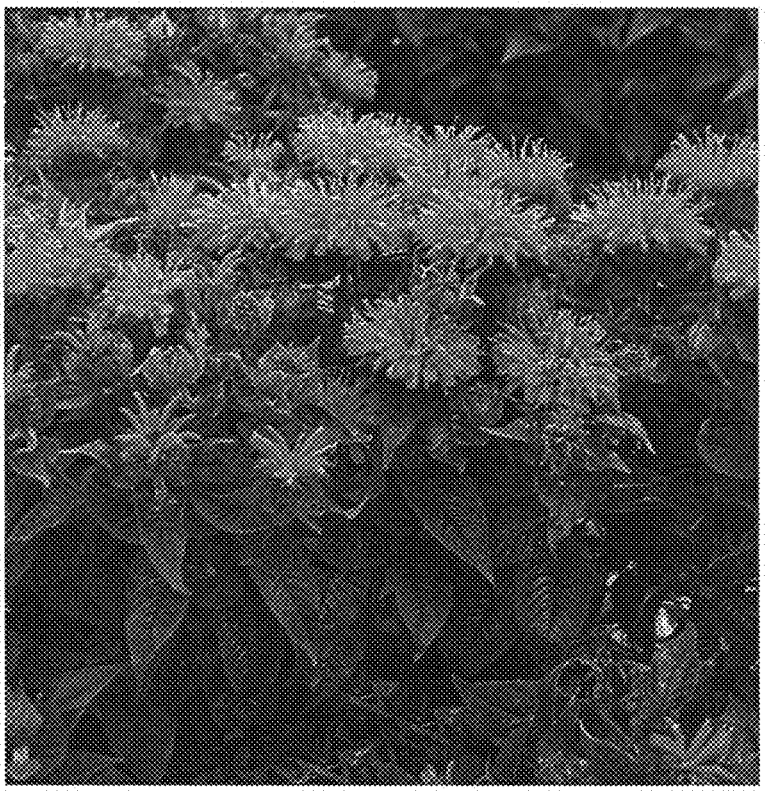
FIG. 2 shows the new plant in flower in the landscape.

The following descriptions and color references are based on the 2001 edition of The Royal Horticultural Society Colour Chart except where common dictionary terms are used. *Monarda didyma* 'Pardon My Cerise' has not been observed under all possible environments. The phenotype may vary slightly with different growing environments such as temperature, light, fertility, soil pH, moisture and maturity levels, but without any change in the genotype. The following observations and size descriptions are based on two-year old greenhouse-grown plants in gallon containers at a nursery in Zeeland, Mich. with supplemental fertilizer and water as needed but without plant growth regulators or pinching.

Botanical classification: *Monarda didyma;*

Parentage: Female (seed) parent is *Monarda didyma* 'Petite Delight' U.S. Plant Pat. No. 10,784; male (pollen) parent is unknown;

Plant habit: Winter-hardy herbaceous perennial, compact, producing several stems spreading by short rhizomes; 35 to 45 cm tall at flowering and 80 to 90 cm wide; flowering begins mid-summer in Michigan and continuing for about 5 to 8 weeks;

Propagation: Stem cuttings;

Time to produce finished crop in 3.8 liter pots: About 10 to 12 weeks; moderate rate of growth;

Root: Fine, fibrous and freely branching; color creamy white to tan depending on soil type;

Leaves: Simple, lanceolate, opposite, serrated, puberulent above and below; lustrous above, matte below; acute apex, rounded to cordate base; 4.0 to 6.5 cm long by 3.0 to 4.0 cm wide, average about 6.0 cm long and 3.5 cm wide;

Leaf color: Young expanding leaves nearest RHS 138C on adaxial surface and on abaxial surface nearest RHS 138D; mature adaxial leaves between RHS 139A and RHS 136A and abaxial leaves nearest RHS 144A;

Foliage fragrance: Pleasantly herbal;

Veins: Pinnate; pubescent below with minute puberulent above, slightly sunken above and raised below;

Vein color: Mature leaves adaxial midrib and primary veins nearest RHS 144D, secondary adaxial veins between RHS 139A and RHS 136A; mature abaxial midrib and primary veins between RHS 145D and RHS 145C, secondary abaxial veins nearest RHS 145B; emerging leaves adaxial midrib and primary veins nearest RHS 138C, secondary veins on emerging abaxial surfaces same color as surrounding leaf tissue; emerging leaves abaxial midrib and primary veins between RHS 145D and RHS 149D, secondary veins on emerging primary abaxial leaves nearest RHS 145B;

Bracts: Between distal leaves and flowers; sessile; deltoid to lanceolate, with acuminate apex and truncate base; about seven per terminal verticillaster; average about 1.6 cm long and 1.0 cm wide;

Bract color: Abaxial and adaxial nearest RHS 145A with veins with heavy tinting of nearest RHS N186C; and veins abaxial and adaxial of nearest RHS 187A;

Petiole: Pubescent, slightly concavo-convex; average about 3.5 mm long and 2.0 mm across;

Petiole color: Nearest RHS 138D with tinting of nearest RHS N187A adaxial and nearest RHS 138D abaxial;

Stems: Quadrangular, puberulent, densely pubescent at nodes and stem corners; about 3.0 mm across at base and about 35 to 45 cm long;

Stem color: Between RHS 138B and RHS 138C in upper portion with base portion blend of between RHS 146C and RHS 138C;

Lower branches: About quadrangular, puberulent, densely pubescent at nodes and stem corners; commonly three to four per main stem; about 2.0 mm across at base and about 30 to 40 cm long;

Lower branch color: Same as main stem with additional tinting of nearest RHS N74C;

Nodes: About 22 to 24 per stem;

Flowers: Single, labiate, actinomorphic flowers arranged in terminal verticillate head about 7.6 cm across and 4.3 cm tall opening from the center and progressing outwardly and down; each flower persisting about 5 days in Michigan; numerous, about 80 flowers per head; flower altitude upright to slightly arcuate in center of verticil to horizontal toward outer perimeter of verticil; self-cleaning;

Flower period: Usually late June into August; about six to seven weeks;

Flower fragrance: Moderately spicy;

Buds one to two days prior to opening: Narrowly oblanceolate; tubular; rounded apex; arcuate slightly downward in distal half; about 2.7 cm long and about 3.0 mm diameter in the middle;

Bud color one to two days prior to opening: Nearest RHS 59C in distal one third with a lighter base of white, lighter than RHS N155D or RHS 155D;

Petals: Labiate, arcuate downward; split in two in about the distal 1.2 cm with upper lip fused into a hood about 3.0 cm long and 2.5 mm diameter; lower lip about 3.5 cm long comprising three lobes including two side lobes about 1.0 mm long with rounded apex and center lobe about 4.0 to 5.0 mm long split in the distal 1.0 mm; both lobes glandular and pubescent outer surfaces with fine hairs the same color as petals; both lobes glabrous on inner surfaces;

Petal color: Color of all petals on both surfaces when first opening nearest RHS 53B with basal 5.0 mm white, lighter than RHS 155D; after about three days open petal color all surfaces between RHS 53D and RHS 54A;

Androecium: Two;

*Filaments*.—Two, about 3.2 cm long by 0.5 mm diameter; color nearest RHS N66D.

*Anther*.—Oblong elliptic, dorsifixed, longitudinal; 2.2 mm by 1.0 mm; color between RHS 62D and RHS 63D with longitudinal dehiscence line between RHS 64C and RHS 64B.

*Pollen*.—Abundant, elliptic to globose, less than 0.1 mm; color nearest RHS 15D.

Gynoecium: One per flower;

*Style*.—About 3.8 cm by 0.25 mm; color between RHS 71D and RHS 71C toward distal end, lightening to nearest RHS 69B toward base.

*Stigma*.—Split in two in the distal 2.0 mm, 0.25 mm in diameter; color nearest RHS 64A.

*Ovary*.—1.0 mm by 0.75 mm; color between RHS 143D and RHS 144B.

Sepals: Five, apiculate apex, base fused forming corolla about 9.0 mm long and 2.0 mm diameter; apex glandular and with minute hairs on abaxial surface;

Sepal color: Abaxial distal one third to half nearest RHS N186C, proximal half to two thirds of outer corolla surface nearest RHS 138C with slight tinting of RHS N186C and darker veins of RHS 138A; and adaxial same colors with veins remaining closer to RHS 138C;

Peduncle: Pubescent, stiff, strong, erect, quadrangular to about 0.3 cm across and average about 38.0 cm long; about 15 per plant; naturally branched at nodes;

Peduncle color: Between RHS 138B and RHS 138C in upper portion with base portion blend of between RHS 146C and RHS 138C;

Fruit: Single nutlet, elliptical, about 1.0 mm long and 0.7 mm wide; color nearest RHS 202A;

Hardiness: The new plant grows best with plenty of moisture and adequate drainage; hardy to at least from USDA zone 4 through 8;

Disease and pest resistance: Demonstrated strong powdery mildew resistance (*Sphaerotheca pannosa* var. *rosa*) in side by side comparison at least equal that of 'Petite Delight' and better than 'AChall'.

We claim:

1. A new and distinct cultivar of ornamental bee balm plant, *Monarda didyma* 'Pardon My Cerise', as herein described and illustrated.

* * * * *